United States Patent
Taranenko et al.

(10) Patent No.: US 7,858,392 B2
(45) Date of Patent: Dec. 28, 2010

(54) METHOD AND APPARATUS FOR PROCESSING OF BIOLOGICAL SAMPLES FOR MASS SPECTROMETRY ANALYSIS

(75) Inventors: Nelli I. Taranenko, Columbia, MD (US); Berk Oktem, Columbia, MD (US); Appavu K. Sundaram, Montgomery Village, MD (US); Vladimir M. Doroshenko, Ellicott City, MD (US)

(73) Assignee: Science and Engineering Services, Inc., Columbia, MD (US)

( * ) Notice: Subject to any disclaimer, the term of this patent is extended or adjusted under 35 U.S.C. 154(b) by 478 days.

(21) Appl. No.: 11/441,176

(22) Filed: May 26, 2006

(65) Prior Publication Data

US 2007/0275478 A1 Nov. 29, 2007

(51) Int. Cl.
*G01N 1/00* (2006.01)
*G01N 35/00* (2006.01)

(52) U.S. Cl. ........................... 436/175; 436/43; 436/174

(58) Field of Classification Search ........................ None
See application file for complete search history.

(56) References Cited

U.S. PATENT DOCUMENTS

| | | | | |
|---|---|---|---|---|
| 5,288,644 | A * | 2/1994 | Beavis et al. | 436/94 |
| 5,705,813 | A * | 1/1998 | Apffel et al. | 250/288 |
| 5,716,825 | A * | 2/1998 | Hancock et al. | 435/286.5 |
| 5,872,003 | A * | 2/1999 | Koster | 435/283.1 |
| 6,140,053 | A * | 10/2000 | Koster | 435/6 |
| 6,225,061 | B1 * | 5/2001 | Becker et al. | 506/16 |
| 6,730,517 | B1 * | 5/2004 | Koster et al. | 436/47 |

OTHER PUBLICATIONS

Online definition of "Virus," Feb. 2010.*

Vladimir M. Doroshenko, et al., "Recent developments in atmospheric pressure MALDI mass spectrometry", International Journal of Mass Spectrometry, vol. 221, 2002, pp. 39-58.

Jimmy K. Eng, et al., "An Approach to Correlate Tandem Mass Spectral Data of Peptides with Amino Acid Sequences in a Protein Database", American Society for Mass Spectrometry, vol. 5, No. 11, 1994, pp. 976-989.

Catherin Fenselau, et al., "Characterization of Intact Microorganisms by Maldi Mass Spectrometry", Mass Spectrometry Reviews, vol. 20, No. 4, 2001, pp. 157-171.

William A. Harris, et al., "On-Probe Digestion of Bacterial Proteins for MALDI-MS", Anal. Chem., vol. 74, No. 17, Sep. 1, 2002, pp. 4410-4416.

Jacob M. Hooker, et al., "Interior Surface Modification of Bacteriophage MS2", J. Am. Chem. Soc., vol. 126, No. 12, 2004, pp. 3718-3719.

(Continued)

*Primary Examiner*—Samuel P Siefke
*Assistant Examiner*—Bryan T Kilpatrick
(74) *Attorney, Agent, or Firm*—Oblon, Spivak, McClelland, Maier & Neustadt, L.L.P.

(57) ABSTRACT

A system and corresponding method for processing of biological samples prior to spectroscopy analysis. The system includes a support for an organic sample, a solution applicator configured to apply a solution for extraction of at least one biomarker protein from the organic sample. The system includes a digester-medium applicator configured to apply to the organic sample a digesting medium capable of at least partial digestion of the biomarker proteins into peptides. The system includes a heating device configured to heat at least one of the organic sample, the solution, the digesting medium, and the biomarker proteins to a temperature above room temperature.

26 Claims, 5 Drawing Sheets

OTHER PUBLICATIONS

M. Karas, et al., "Laser Desorption Ionization of Proteins with Molecular Masses Exceeding 10 000 Daltons", Anal. Chem UMCP, vol. 60, No. 20, Oct. 15, 1988, pp. 2299-2301.

Thaiya Krishnamurthy, et al., "Rapid Identification of Bacteria by Direct Matrix-assisted Laser Desorption/Ionization Mass Spectrometric Analysis of Whole Cells", Rapid Communications in Mass Spectrometry, vol. 10, 1996, pp. 1992-1996.

Andrew N. Krutchinsky, et al., "Automatic Identification of Proteins with a MALDI-Quadrupole Ion Trap Mass Spectrometer", Anal. Chem., vol. 73, Nov. 1, 2001, pp. 5066-5077.

David N. Perkins, et al., "Probability-based protein identification by searching sequence databases using mass spectrometry data", Electrophoresis, vol. 20, No. 18, 1999, pp. 3551,3567.

Patrick A. Pribil, et al., "Rapid characterization of bacillus spores targeting species-unique peptides produced with an atmospheric pressure matrix-assisted laser desorption/ionization source", Journal of Mass Spectrometry, vol. 40, No. 4, 2005, pp. 464-474.

James H. Strauss, Jr., et al., "Purification and Properties of Bacteriophage MS2 and of its Ribonucleic Acid", J. Mol. Biol., vol. 7, 1963, pp. 43-54.

Koichi Tanaka, et al., "Protein and Polymer analyses up to m/z 100 000 by Lazer Ionization Time-of-flight Mass Spectrometry", Rapid Communications in Mass Spectrometry, vol. 2, No. 8, 1988, pp. 151-153.

Bettina Warscheid, et al., "Characterization of Bacillus Spore Species and Their Mixtures Using Postsource Decay with a Curved-Field Reflectron", Anal. Chem., vol. 75, No. 20, Oct. 15, 2003, pp. 5618-5627.

\* cited by examiner

METHOD AND APPARATUS FOR PROCESSING OF BIOLOGICAL SAMPLES FOR MASS SPECTROMETRY ANALYSIS

CROSS REFERENCE TO RELATED APPLICATIONS

This application is related to U.S. Ser. No. 11/441,175, filed May 26, 2006, entitled "On-probe Sample Cleanup System and Method for MALDI Analysis," the entire contents of which are incorporated herein by reference.

DISCUSSION OF THE BACKGROUND

1. Field of the Invention

This invention relates to the field of biochemical analysis by mass spectrometry. More specifically this invention relates to the optimization of biological sample processing for mass spectrometric analysis; in particular for biological agent sample preparation for mass spectrometric analysis using matrix assisted laser desorption/ionization (MALDI) ion sources or atmospheric pressure MALDI ion sources for generation of ions.

2. Background of the Invention

Mass spectrometry has been used to analyze microorganisms. Biomarkers, cellular material specific to these microorganisms, such as proteins and peptides have been found to be characteristic of a given organism such as bacterial spores or viruses. Toxins are proteins and are analyzed similarly.

MALDI mass spectrometry (MS) has been used for the analysis of biomolecules with large molecular weight. MALDI techniques can detect molecular ions with masses greater than 100,000 Da. MALDI is suitable for analyzing complex mixtures (without prior mixture separation) and for this reason it is considered as a suitable technique for peptide/protein characterization.

Organism specific biomarkers (usually proteins or peptides) have been identified using various combinations of sample processing techniques and identified by mass spectrometry. In order for mass spectrometry to produce the signals of these biomarkers, the microorganisms should be purified from the rest of the cellular material that is present. This is usually followed by sample concentration. Chromatography is commonly used for these purposes with the separation usually taking more than 15-30 minutes. After separation, the microorganism samples are typically treated with enzymes to provide biomarker peptides that can be analyzed by mass spectrometry or tandem mass spectrometry (or MS/MS).

The resultant tandem mass spectral data are typically provided to a proteomic database search, and the organisms are identified from the particular protein returned by the database. Proteomic databases are utilized for comparison to and identification of proteins based on comparison of peptide sequence information obtained in the MS/MS analysis with those available in the proteome/genome database and subsequently provide the identification of the protein and then the organism.

In the case of MALDI or atmospheric pressure (AP) MALDI, a separation step is not necessary, and biological samples are processed on a sample holder (e.g., a probe or a MALDI target plate). The biological samples may be selectively dissolved, or in the case of whole cells the cells may be lysed on the plate releasing the biomarkers. This sample processing, combined with MALDI analysis can provide protein signatures which can be matched to the genome of a specific biological entity or bacteria. This permits identification of microorganisms, which can also be used as biomarkers of common functional diseases and disorders. Sequence determination of such biomarkers can be achieved with high throughput.

The following articles related to sample preparation, processing, and analysis have been reported in the scientific literature, all of which are incorporated herein in entirety by reference:

1. Doroshenko, V. M.; Laiko, V. V.; Taranenko, N. I.; Berkout, V. D.; Lee, H. S. (2002), "Recent developments in atmospheric pressure MALDI mass spectrometry" Int. J. Mass Spectrom. 221: 39-58.
2. Eng, J. K., A. L. McCormack, et al. (1994). "An approach to correlate tandem mass spectral data of peptides with amino acid sequences in a protein database." Journal of the American Society for Mass Spectrometry 5(11): 976-989.
3. Fenselau, C. and P. A. Demirev (2001). "Characterization of intact microorganisms by MALDI mass spectrometry." Mass Spectrom. Rev. 20(4): 157-171.
4. Harris, W. A. and J. P. Reilly (2002). "On-Probe Digestion of Bacterial Proteins for MALDI-MS" Anal. Chem. 74(17): 4410-4416.
5. Hooker, J. M., E. W. Kovacs, and M. B. Francis, Interior surface modification of bacteriophage MS2. J Am Chem Soc, 2004. 126(12): p. 3718-9.
6. Karas, M. and F. Hillenkamp (1988). "Laser desorption ionization of proteins with molecular masses exceeding 10000 Daltons." Anal. Chem. 60(20): 2299-2301.
7. Krishnamurthy, T. and P. L. Ross (1996). "Rapid identification of bacteria by direct matrix-assisted laser desorption/ionization mass spectrometric analysis of whole cells." Rapid Commun. Mass Spectrom. 10: 1992-1996.
8. Krutchinsky, A. N., M. Kalkum, et al. (2001). "Automatic Identification of Proteins with a MALDI-Quadrupole Ion Trap Mass Spectrometer." Anal. Chem. 73: 5066-5077.
9. Perkins, D. N., D. J. Pappin, et al. (1999). "Probability-based protein identification by searching sequence databases using mass spectrometry data." Electrophoresis 20(18): 3551-67.
10. Pribil P A, Patton E, Black G, Doroshenko V, Fenselau C. (2005), "Rapid characterization of *Bacillus* spores targeting species-unique peptides produced with an atmospheric pressure matrix-assisted laser desorption/ionization source." J Mass Spectrom. 40(4): 464-474.
11. Strauss, J. H., Jr. and R. L. Sinsheimer, Purification and properties of bacteriophage MS2 and of its ribonucleic acid. J Mol Biol, 1963. 7: p. 43-54.
12. Tanaka, K., H. Waki, et al. (1988). "Protein and polymer analyses up to m/z 100,000 by laser ionization time-of-flight mass spectrometry." Rapid Commun. Mass Spectrom. 2: 151-153.
13. Warscheid, B., and Fenselau, C. (2003). "Characterization of *Bacillus* Spore Species and Their Mixtures Using Postsource Decay with a Curved-Field Reflectron," Anal. Chem. 75(20): 5618-5627.

Despite this work, improved sample preparation and processing techniques are still being pursued.

SUMMARY OF THE INVENTION

Accordingly, one object of the present invention accomplished in various of the embodiments is to provide a system (and corresponding method) for processing of organic samples prior to spectroscopy analysis.

Another object of the present invention accomplished in various of the embodiments is to provide a system (and corresponding method) for analysis of microorganisms.

Yet another object of the present invention accomplished in various of the embodiments is to provide a system (and corresponding method) for proteins and toxins.

Various of these and other objects are provided for in certain ones of the embodiments of the present invention.

In one embodiment of the present invention, there is provided a system for processing of organic samples prior to spectroscopy analysis. The system includes a support for an organic sample and a solution applicator configured to apply a solution for extraction of at least one biomarker protein from the sample. The system includes a digester-medium applicator configured to apply to the sample a digesting medium capable of at least partial digestion of the biomarker proteins into peptides. The system includes a heating device configured to heat at least one or all of the organic sample, the solution, the digesting medium, and the biomarker proteins to a temperature above room temperature.

In one embodiment of the present invention, there is provided a method for processing of biological samples prior to spectroscopy analysis. The method deposits on a support an organic sample, applies a solution to the sample for extraction of at least one biomarker protein from the organic sample, applies to the sample a digesting medium capable of at least partial digestion of the biomarker proteins into peptides, and heats at least one of the organic sample, the solution, the digesting medium, and the biomarker proteins to a temperature above room temperature.

It is to be understood that both the foregoing general description of the invention and the following detailed description are exemplary, but are not restrictive of the invention.

BRIEF DESCRIPTION OF THE DRAWINGS

A more complete appreciation of the present invention and many attendant advantages thereof will be readily obtained as the same becomes better understood by reference to the following detailed description when considered in connection with the accompanying drawings, wherein.

DETAILED DESCRIPTION OF THE INVENTION

On probe sample processing combined with sequencing by mass spectrometry can characterize organic samples such as for example bacteria, bacterial spores, viruses and toxins and can even distinguish closely related bacteria at the species and strain level. Conventionally, the total analysis time (including sample processing and mass analysis) takes typically from 10-20 min. The sample processing occupies almost all of this time. Sample processing in general includes several steps such as protein biomarker extraction (usually using specific solvent), protein digestion, on-probe sample cleanup, and MALDI matrix deposition and usually includes several steps of sample liquid evaporation. While each individual step can be accelerated by using different methods and optimizing different parameters, the problem of minimizing the total processing time becomes very complicated since many parameters can be involved in each step and those parameters may have different optimal values for different steps.

Faster techniques combining sample processing and sample preparation with MALDI analysis are desirable to fully exploit the speed of the MALDI analysis. In one embodiment of the present invention, the sample preparation time can be minimized by processing the sample directly on the sample holder (i.e., a probe or a MALDI plate).

In one aspect of the present invention, the problem of minimizing the processing process is addressed by selecting and optimizing the sample temperature, to thereby decrease the process time. The present invention utilizes the discovery that increasing the sample (or sample support) temperature beyond 50° C. increases the rate of all individual steps involved, while the protein/peptide biomarker molecules and biological reagents involved in the sample processing (like trypsin enzyme) still remain intact and retain their biological activity sufficient for successful microorganism (or toxin) identification. For example, at 37° C. this type of analysis takes more than 10 minutes per sample. At 60° C., it can be done in 2 minutes due to an increase in evaporation rate. Hence, in one embodiment of the present invention, elevated on probe sample processing can reduce the sample processing time to 5 minutes or below.

Figure 1A:
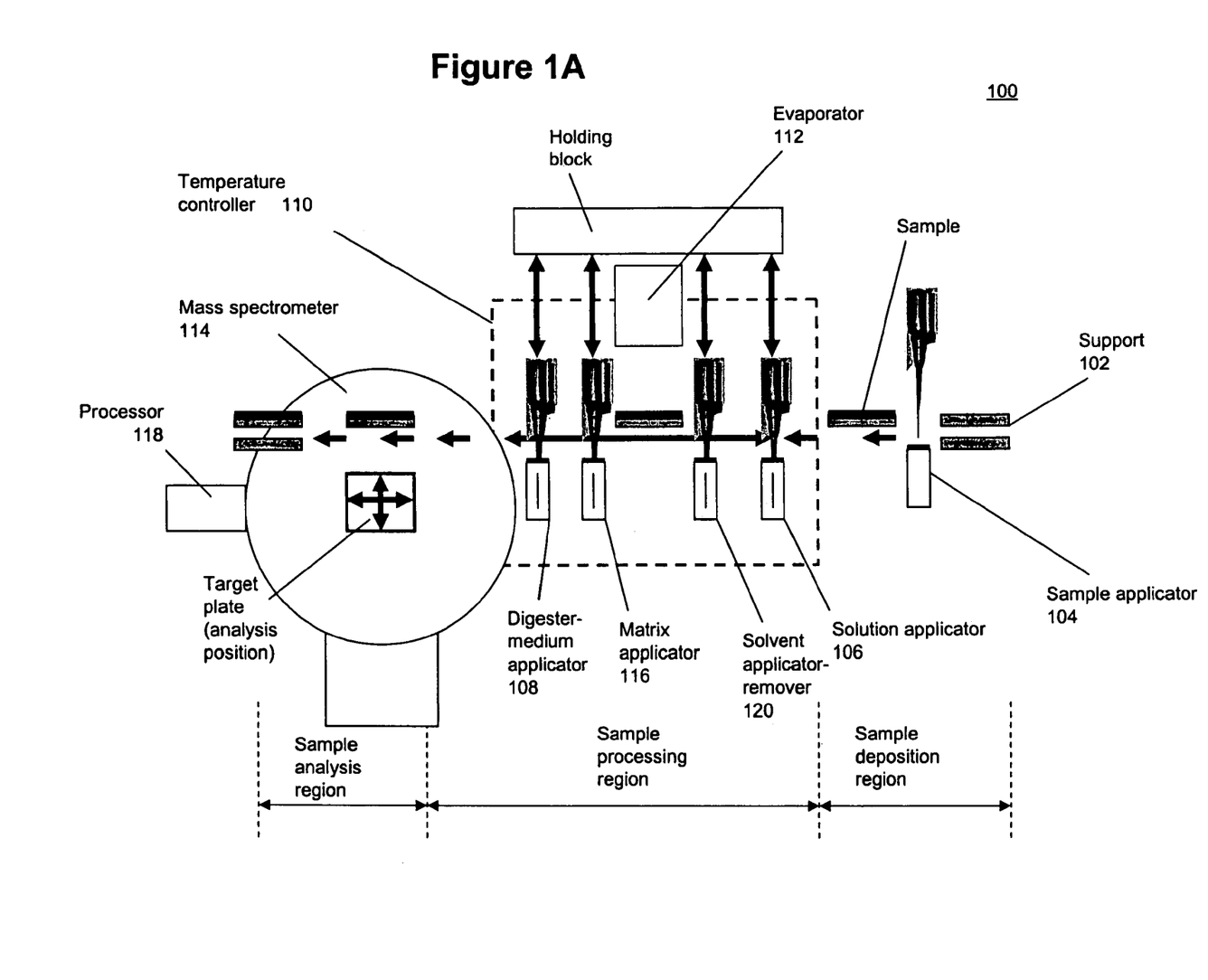
FIG. 1A is a schematic illustration of a system, according to one embodiment of the present invention, for processing of biological samples prior to spectroscopy analysis.

Referring now to the drawings, wherein like reference numerals designate identical, or corresponding parts throughout the several views, and more particularly to FIG. 1A, FIG. 1A is a schematic illustration of a system 100 for processing of biological samples prior to spectroscopy analysis. As shown in FIG. 1A, the system 100 includes a support 102 for an organic sample. The system 100 as shown in FIG. 1A can include a sample applicator 104 for application of the organic sample to the support 104. In one embodiment of the present invention, the sample applicator 104 can apply one of a protein sample, a peptide sample, an oligosaccharide sample, a DNA sample, a RNA sample, a lipid sample, a phospholipids sample, a spore, a bacteria, a virus, a toxin, or a combination these and other organic materials. Suitable sample applicators can be manual or automated dispensers including for example pipettor or automated sample dispensing units. The sample applicator can be configured (through conventional metering controls and feeds) to supply the liquid sample to the support 102.

The support 102 can be a MALDI support or a MALDI target plate, which can be a gold surface, a silver surface, a polymer surface, a hydrophobic surface, a hydrophilic surface, a polytetrafluoroethane surface, a metallic surface, a dielectric surface, a stainless steel surface, or a combination of these surfaces.

As shown in FIG. 1, the system 100 includes a solution applicator 106 for application of a solution for extraction of one or more biomarker proteins from the organic sample. The solution applicator 106 can apply an acid or a base solution for extraction of the biomarker proteins. In one embodiment of the present invention, when a spore is applied as the organic sample, the acid extracts as the biomarker protein a protein from the small acid-soluble protein (SASP) family. Acid solutions such as for example trifluoroacetic acid (TFA) can be applied by the solution applicator for this and other extractions. Formic acid or acetic acid are applicable as well for this type of extraction as these acids are volatile and can be removed by evaporation subsequently. The extracted biomarker protein can be SAS2_BACSU (Mass: 7332 Small, acid-soluble spore protein 2 (SASP-2).—*Bacillus subtilis*) as given in Mass Spectrometry protein sequence Data Base (MSDB) database compiled by the Proteomics Group at Imperial College London.

In other applications, a virus, bacteria, a spore, a toxin, or a combination thereof can be applied as the organic sample, and ammonium hydroxide or tris-carbonate or a combination thereof can be applied as a base for extraction of the biomarker proteins. Tris buffer or NaOH are also applicable to extract this class of biomarkers such as 1AQ3A from MSDB database. (Mass: 13714 ms2 protein capsid mutant T59S, chain A—phage ms2).

As shown in FIG. 1A, the system 100 includes a digester-medium applicator 108 for application to the organic sample a digesting medium capable of at least partial digestion of the biomarker proteins into peptides. The digester-medium applicator can be configured (through conventional metering controls and feeds) to supply a predetermined amount of the digesting medium to the support 102. The digesting medium can include one or more enzymes such as trypsin, subtilisin, chymotrypsin, pepsin, papain, *S. aureus* V8, elastase, Lys-C endoproteinase, Arg-C endoproteinase, and Glu-C endoproteinase enzymes. The enzymes can be immobilized on tiny beads or surface to minimize autolysis.

As shown in FIG. 1A, the system 100 includes a temperature controller 110 configured to heat at least one of the organic sample, the solution, the digesting medium, and the biomarker proteins to a temperature above 50° C. The temperature controller 110 can be configured to maintain the temperature above 60° C. or above 67° C. The temperature controller 110 can include one or more of a hot plate, a radiative heater, a light heater, a laser heater, or a microwave heater. In some embodiments of the present invention, the temperature exceeds above 67° C. which is above the recommended temperature from the enzyme manufacturer. In one embodiment of the present invention, 80° C. is considered a practical upper range suitable for many of the biological samples. Above 100° C. this method is not as feasible due to the rapid evaporation of the liquid organic samples before the samples can be dispersed on the support 102. While the temperature controller 110 is shown illustratively in FIG. 1A as being in the sample processing region, the temperature controller 110 in one embodiment can be enlarged to provide temperature control in the sample deposition and sample analysis regions. The temperature controller 110 may be segmented to provide different temperature control in different regions of the system 100.

As shown in FIG. 1A, in one embodiment of the present invention, the system 100 optionally includes an evaporator 112. The evaporator 112 is configured to evaporate liquid from the support. The evaporator 112 can be a forced gas evaporator, a forced air evaporator, a reduced pressure evaporator, and a heated evaporator. The evaporator 112 in one embodiment of the present invention can operate in conjunction with the heating device 110. While the evaporator 112 is shown for illustrative purposes in the sample processing region, the evaporator 112 can be located at other positions in the system 100, such as in the sample deposition region.

As shown in FIG. 1A, in one embodiment of the present invention, the system 100 optionally includes a mass spectrometer 114 for performing spectroscopic identification of the biological marker proteins or peptides in the organic sample. The mass spectrometer 114 can be a tandem mass spectrometer or an ion mobility spectrometer. Such spectrometers for example can be a MALDI mass spectrometer, a MALDI tandem mass spectrometer, a MALDI ion mobility spectrometer, an AP-MALDI mass spectrometer, an AP-MALDI tandem mass spectrometer, or an AP-MALDI ion mobility spectrometer.

As shown in FIG. 1A, in one embodiment of the present invention, the system 100 optionally includes a matrix applicator 116 configured to apply, for assistance in laser desorption ionization, a matrix solution to the organic sample. The matrix applicator 116 can be a manual or a robotic dispenser of a matrix solution. Suitable matrix solutions are α-cyano-4-hydroxycinnamic acid, 2,5-dihydroxybenzoic acid, sinapinic acid, ferulic acid, or a combination of the acids.

As shown in FIG. 1A, in one embodiment of the present invention, the system 100 optionally includes a processor 118. The processor 118 can direct the mass spectrometer 114 and is programmed with software to compare the peptide fragment data with a protein sequence database including known microorganism protein/peptide sequences or genomic sequences, and to identify the microorganism/agent by matching the at least one biomarker with results generated from proteomic interpretation of the microorganism proteome/genome. Software that is used for this purpose can be MASCOT which is available to use for free at http://www-.matrixscience.com to do single searches. It does connect to major protein databases such as NCBInr, Swissprot or MSDB which is accessible through the MASCOT search engine.

As shown in FIG. 1A, the system 100 can include a solvent applicator-remover 120 for application of a solvent for dissolution of the contaminants in the liquid sample once evaporated. The solvent applicator-remover 120 can remove the applied solvent from the evaporated sample, thereby removing at least a part of the contaminants. In certain cases, greater than 95% of contamination can be removed. Examples of contaminants removed include buffer salts, detergents, components of media used for growing cells, environmental or dust particles present in the bioaerosol collection, while retaining concentrations of proteins, peptides, lipids and toxins extracted from microorganisms or cells for analyte analysis. Suitable solvent applicators can be manual or automated dispensers including for example a solvent pipettor or dispenser. The solvent applicator 120 can be configured (through conventional metering controls and feeds) to supply the solvent to the support 102.

Suitable solvents include water, a volatile buffer like ammonium bicarbonate buffer, a non-volatile buffer such as tris-buffer, and phosphate buffered saline (PBS), organic solvents, ethanol, methanol, isopropanol, acetone, and/or acetonitrile. Other solvents that can be used in the present invention are described in above-noted related application entitled "On-probe Sample Cleanup System and Method for MALDI Analysis".

Figure 1B:
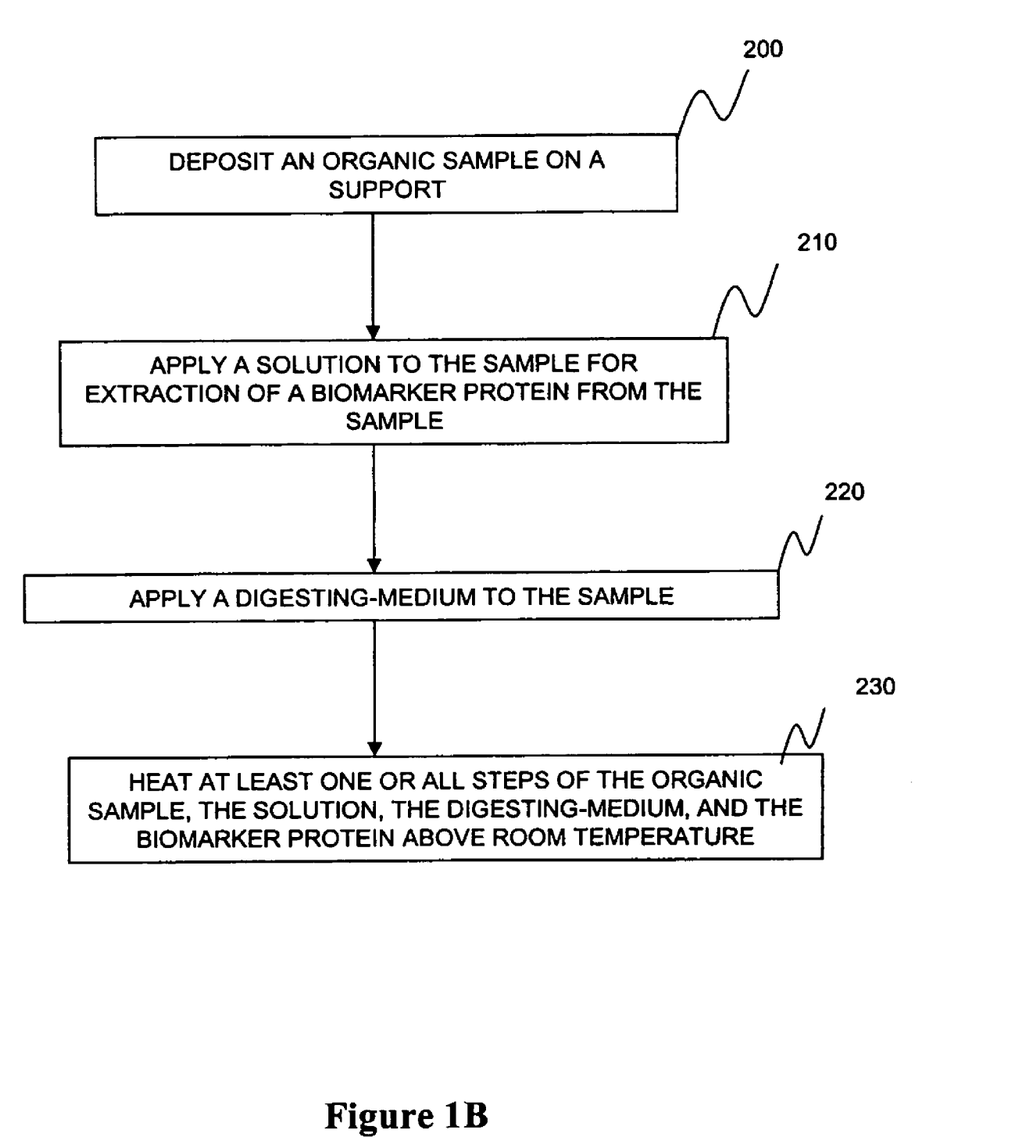
FIG. 1B is a schematic illustration of a method, according to one embodiment of the present invention, for processing of biological samples prior to spectroscopy analysis.

FIG. 1B depicts a detailed flowchart according to one embodiment of the present invention of a method for processing of biological samples prior to spectroscopy analysis. At 200, an organic sample is deposited on a support. At 210, a solution is applied to the sample for extraction of at least one biomarker protein from the organic sample. At 220, a digesting medium is applied to the sample that is capable of at least partial digestion of the biomarker proteins into peptides. At 230, at least one of the organic sample, the solution, the digesting medium, and the biomarker proteins are heated to a temperature above room temperature.

At 230, as discussed in more detail elsewhere, the heating procedures of the present invention in one embodiment maintain the temperature above 50° C., or above 67° C., or in a range from 50 to 80° C.

At 200, the sample deposited for processing can include a biological agent, a microorganism, a cell culture, a protein sample, a peptide sample, an oligosaccharide sample, a DNA sample, a RNA sample, a lipid sample, a phospholipids sample, a spore, a bacteria, a virus, a toxin, or a combination these samples. After processing, mass spectroscopy is performed on the sample using the mass spectrometer discussed above for tandem mass spectroscopy or ion mobility spectroscopy. To assist in mass analysis, a matrix solution (such as those described above) can be applied to the digested sample.

To assist in sample preparation, liquid from the support can be evaporated in one embodiment of the present invention by forced gas evaporation, forced air evaporation, reduced pressure evaporation, and/or heated evaporation techniques. To assist in sample preparation, an acidic or a basic solution can be applied to the sample to extract biomarkers. More generally, various solvents (as discussed above) can be applied to the sample dissolution of contaminants in the sample, and removal of the applied solvent from the sample serves to remove at least a part of the contaminants.

To assist in sample preparation, at 220, the applied digesting medium enzymes such trypsin, subtilisin, chymotrypsin, pepsin, papain, S. aureus V8, elastase, Lys-C endoproteinase, Arg-C endoproteinase, and Glu-C endoproteinase enzymes, or combination of these enzymes.

Moreover, mass spectroscopy can be performed on the samples with the resultant date being compared with a protein sequence database. By comparing the mass analysis data to known microorganism protein/peptide sequences or genomic sequences, a microorganism/agent can be identified for example by matching the detected biomarkers with results generated from proteomic interpretation of a microorganism proteome/genome.

The above-described methods of the present invention are straightforward and do not require fractionation or protein isolation steps. Samples can be processed directly on a sample support, for example, on a MALDI sample plate in a time frame of approximately 2 to 10 min (using for example the elevated temperature conditions described above) or comparison, it takes an aqueous droplet with a volume of 1 µl more than 4 minutes to dry at room temperature. Several of these drying steps are required for sample processing. Therefore sample preparation without additional heating takes longer than 20 minutes.

At least one biomarker protein/peptide can be extracted from the sample. The sample solution evaporates almost instantly under these elevated temperature conditions. The sample can then be treated with enzymes. The proteins are subsequently digested into peptides. Above 60° C., the processes of extracting, evaporating and digesting are also accelerated.

Following the digestion, a matrix solution can be applied to the sample. The elevated temperature also accelerates the drying of the matrix solution. Prior to the advent of immobilized enzymes, attempts to increase the temperature at which the samples were prepared simply did not work because trypsin autolysis products dominated the mass spectra. The present invention has recognized that the immobilized enzymes digest the proteins at elevated temperatures without destroying itself (autolysis) and proteins remain in a form that can be readily extracted from the organic sample prior to mass analysis.

The following examples are given for the purpose of illustrating various embodiments of the invention and are not intended to limit the present invention in any fashion.

Equipment and Materials

Molecular Biology Grade water was purchased from Biowittaker (Walkersville, Md.). α-cyano-4-hydroxycinnamic acid (CHCA) was obtained from Fluka (Buch, Switzerland). All other chemicals—Trifluoroacetic acid (TFA), $NH_4OH$, Ovalbumin—were purchased from Sigma Chemical Co. (St. Louis, Mo.) and used without further purification. Immobilized trypsin beads (Poroszyme Bulk Immobilized Trypsin) were purchased from Applied Biosystems (Foster City, Calif., USA) and used washed with 50 mM ammonium bicarbonate three times prior to being resuspended in a volume of 2.5 times the original volume prior to use.

*Escherichia coli* bacteriophage MS2 was purchased from ATCC (Manassas, Va.) along with the host *Escherichia coli* strain C3000. MS2 bacteriophage was propagated and purified according to the existing procedures (e.g., those described by Hooker et. al 2004 and Strauss et. al. 1963). Spores of *Bacillus globigii* were obtained from the US government.

Mass spectral experiments were carried out on a Thermo Finnigan (San Jose, Calif., USA) LCQ Deca XP ion trap mass spectrometer integrated with an AP/MALDI ion source (MassTech Inc. Columbia, Md.). Matrix-assisted laser desorption ionization was attained with a nitrogen laser ($\lambda$=337 nm, a Spectra-Physics, Mountain View, Calif., Model 337 Si). Samples were placed, processed, and desorbed/ionized from a gold-plated stainless steel target plates (MassTech Inc.). HPLC-grade solvents were purchased from Fisher Scientific, Inc. (Pittsburgh, Pa.). The MALDI matrix was prepared as a 50 mM CHCA solution in 70% acetonitrile/0.1% TFA.

The temperature of the target plate with a sample on it was controlled using a high accuracy hotplate. (SP136425Q, Barnstead International, Dubuque, Iowa). In experiments with radiative heating of the sample, a compact desk lamp with 120 W output light bulb was used. The lamp was kept at a distance of several centimeters to the plate to allow sample temperature control. Temperature of the plate under the lamp is measured at the surface and at the interior of the plate by having a hole drilled from the side of the AP-MALDI target plate with a 1 mm diameter thermocouple inserted 1 cm into the hole with maximum contact.

Example 1

An aliquot of 1 µl of aqueous suspension of *Bacillus Globigii* (BG) spores (2.5 mg/ml) was placed on a MALDI sample holder and mixed with 1 µl diluted TFA (10% in water). The mixture was allowed to dry before addition of 1 µl of trypsin solution. This trypsin solution contained immobilized trypsin on 20 µm diameter beads in 50 mM $NH_4HCO_3$ buffer solution. The sample was incubated for the length of natural evaporation of the trypsin solution. Digestion was stopped by allowing the sample to dry followed by the addition of 1 µl of the CHCA matrix solution. The matrix solution, α-cyano-4-hydroxycinnamic acid (50 mM in 70% acetonitrile/0.1% TFA), was placed on the digested spore sample to facilitate MALDI mass spectrometric analysis.

The temperature was controlled both by a hotplate and/or a radiative heat source. At room temperature (25° C.) the duration of this experiment was more than 30 minutes. However, at elevated temperatures of such as 70° C., complete sample processing took less than 2 minutes.

Figure 2:
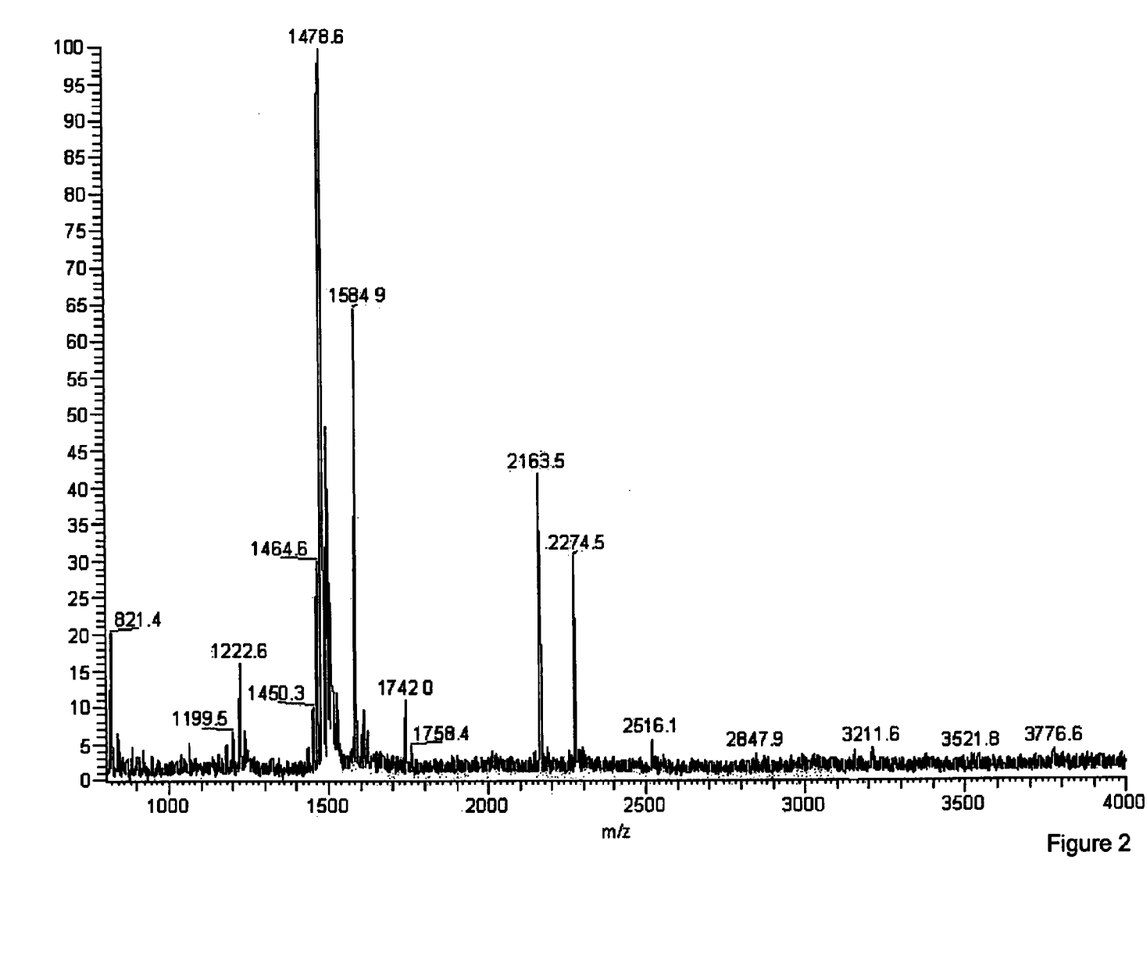
FIG. 2 is a mass spectrum for on probe digested bacterial spore Bacillus globigii prepared according to one embodiment of the present invention with a hot plate at 70° C.

After processing, the sample was analyzed using AP-MALDI/LCQ in the MS mode. FIG. 2 shows the mass spectrum obtained with hotplate set at 70° C. The peaks are identified as peptides resulting from tryptic digestion of small acid soluble proteins of BG spores. In similar setup (results not shown) a lamp (described above) is used as heat source with comparable results.

Example 2

An aliquot of 1 μl aqueous suspension of MS2 virus ($10^{-6}$ pfu) was placed onto a MALDI sample plate and mixed with 1 μl of diluted $NH_4OH$ (50% in water). The mixture was allowed to dry before addition of 1 μl of trypsin solution. This trypsin solution contained immobilized trypsin on 20 μm diameter beads in $NH_4HCO_3$ buffer solution. The sample was incubated for the length of evaporation of the trypsin solution. Digestion was stopped by allowing the sample to dry followed by the addition and drying of 1 μl of the matrix solution.

The temperature in this experiment is controlled both by a hotplate and/or a radiative heat source. At room temperature (25° C.) the duration of this experiment was more than 30 minutes. However, at elevated temperatures such as 70° C., the overall processing took less than 2 minutes.

Figure 3:
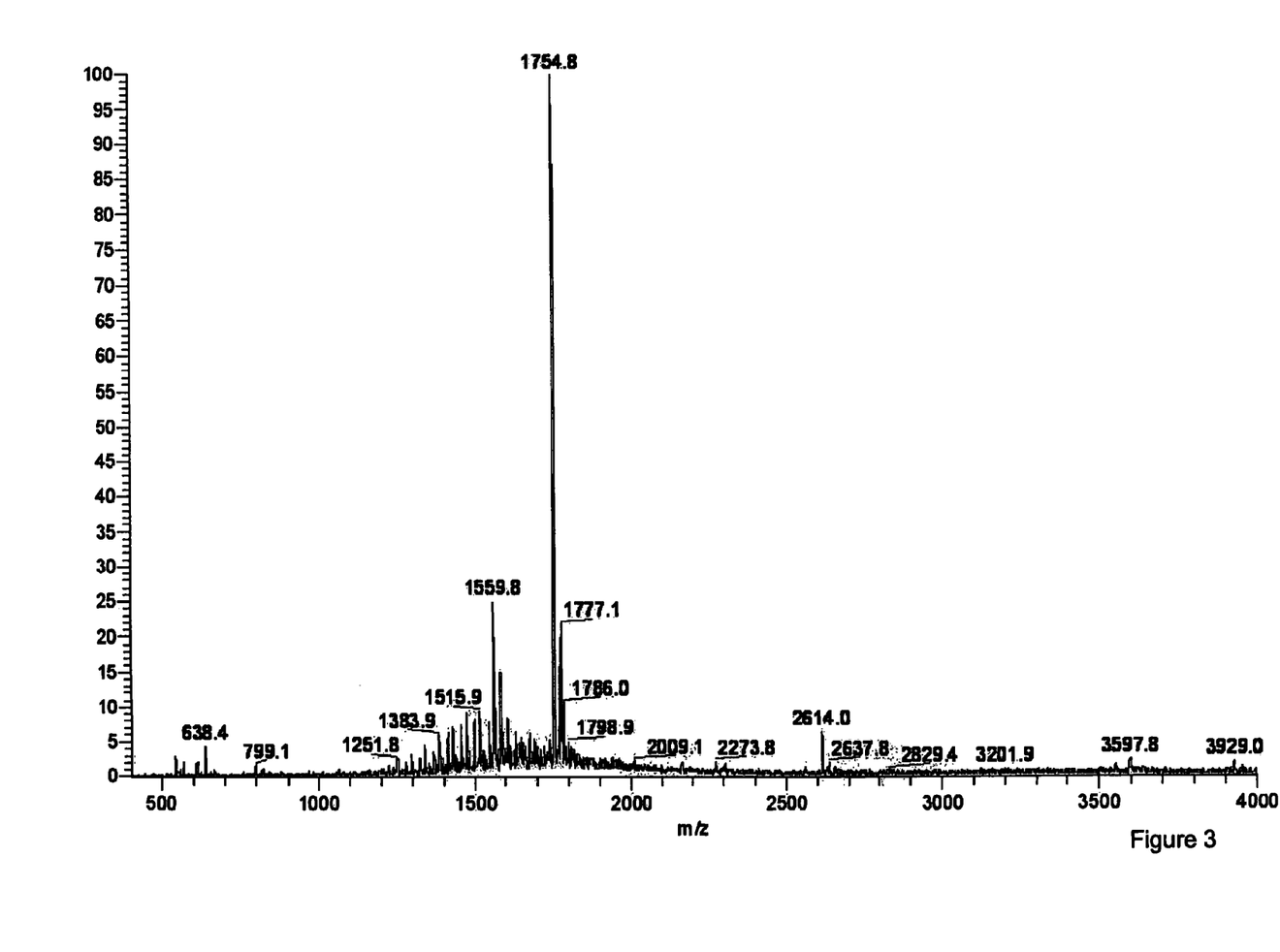
FIG. 3 is a mass spectrum for on probe digested virus MS2 prepared according to one embodiment of the present invention with a hot plate at 70° C.

After processing the sample was analyzed using AP-MALDI/LCQ in the MS mode. FIG. 3 shows the mass spectrum obtained from this experiment 2 with hotplate set at 70° C. The peaks are identified as peptides obtained from tryptic digestion of MS2 capsid protein. In similar setup (results not shown) a lamp (described above) is used as heat source with comparable results.

Example 3

An aliquot of 1 μl aqueous suspension of Ovalbumin (1 mg/ml) was placed onto a MALDI sample plate. The sample droplet dried almost simultaneously at 70° C. Then 1 μl of trypsin solution was added. This trypsin solution contained immobilized trypsin on 20 μm diameter beads in $NH_4HCO_3$ solution. The sample was incubated for the length of evaporation of the trypsin solution. Digestion was stopped by allowing the sample to dry followed by the addition and drying of 1 μl of the matrix solution.

The temperature in this experiment was controlled both by a hotplate and/or a radiative heat source. At room temperature (25° C.), the duration of this experiment was more than 30 minutes. However, at elevated temperatures such as 70° C., the overall processing took less than 5 minutes.

Figure 4:
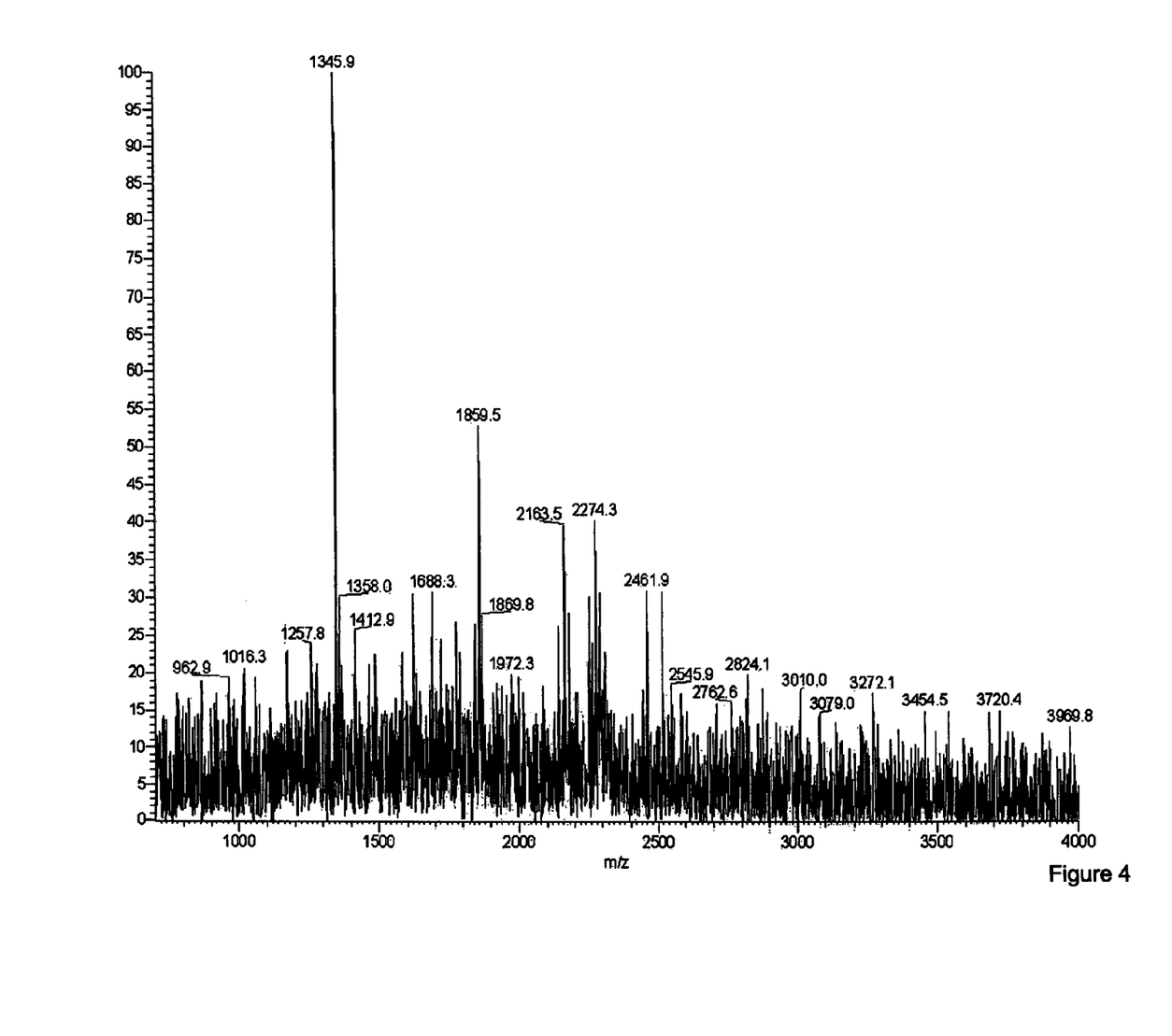
FIG. 4 is a mass spectrum for on probe digested toxin simulant Ovalbumin prepared according to one embodiment of the present invention with a hot plate at 70° C.

After processing the sample was analyzed using AP-MALDI/LCQ in the MS mode. FIG. 4 shows the mass spectrum obtained with the hotplate set at 70° C. The peaks are identified as peptides formed by tryptic digestion of Ovalbumin. In similar setup (results not shown), a lamp (described above) is used as heat source with comparable results.

Numerous modifications and variations on the present invention are possible in light of the above teachings. It is, therefore, to be understood that within the scope of the accompanying claims, the invention may be practiced otherwise than as specifically described herein.

The invention claimed is:

1. A system for processing of organic samples prior to spectroscopy analysis, comprising:
a support for an organic sample;
a sample applicator configured to apply the organic sample to the support;
a solution applicator configured to apply a solution for extraction of at least one biomarker protein from the organic sample;
a digester-medium applicator configured to apply to the organic sample a digesting medium capable of at least partial digestion of the biomarker proteins into peptides; and
at least one heating device in a temperature controlled region including the digester-medium applicator, the at least one heating device configured to heat at a position different from a spectroscopy analysis position at least two or all of the organic sample, the solution, the digesting medium, and the biomarker proteins to a temperature above room temperature,
wherein the support for the organic sample moves in relation to the at least one heating device, and
the sample and the digestion medium are applied at separate locations along a direction of motion of the support, with the sample applied to the support in a position other than in the temperature controlled region of the digester-medium applicator.

2. The system as in claim 1, wherein the at least one heating device is configured to maintain the temperature above 50° C.

3. The system as in claim 1, wherein the at least one heating device is configured to maintain the temperature above 67° C.

4. The system as in claim 1, wherein the at least one heating device is configured to maintain the temperature in a range from 50 to 80° C.

5. The system as in claim 1,
wherein the sample applicator is configured to apply to the support at least one of a biological agent, a microorganism, a cell culture, a protein sample, a peptide sample, an oligosaccharide sample, a DNA sample, a RNA sample, a lipid sample, a phospholipids sample, a spore, a bacteria, a virus, a toxin, or a combination thereof.

6. The system as in claim 1, further comprising:
at least one of an ion mobility spectrometer, a mass spectrometer, or a tandem mass spectrometer.

7. The system as in claim 6, wherein the mass spectrometer comprises:
at least one of a MALDI mass spectrometer, a MALDI tandem mass spectrometer, a MALDI ion mobility spectrometer, an AP-MALDI mass spectrometer, an AP-MALDI tandem mass spectrometer, or an AP-MALDI ion mobility spectrometer.

8. The system as in claim 1, further comprising:
a matrix applicator configured to apply, for assistance in laser desorption ionization, a matrix solution to the sample.

9. The system as in claim 8, wherein the matrix solution includes at least one of α-cyano-4-hydroxycinnamic acid, 2,5-dihydroxybenzoic acid, sinapinic acid, ferulic acid, or a combination thereof.

10. The system as in claim 1, further comprising:
an evaporator configured to evaporate liquid from the support.

11. The system as in claim 10, wherein the evaporator comprises at least one of a forced gas evaporator, a forced air evaporator, a reduced pressure evaporator, and a heated evaporator.

12. The system as in claim 10, wherein the at least one heating device comprises the evaporator.

13. The system as in claim 1, wherein the solution applicator is configured to apply an acidic solution.

14. The system as in claim 13,
wherein the sample applicator is configured to apply a spore to the support as the organic sample; and
the solution applicator is configured to apply a solution that extracts a protein from the small acid-soluble protein (SASP) family.

15. The system as in claim 14, wherein the solution applicator is configured to apply a trifluoroacetic acid (TFA) solution as the acid solution.

16. The system as in claim 1, wherein the solution applicator is configured to apply a basic solution.

17. The system as in claim 16, wherein:
the sample applicator is configured to apply to the support as the sample at least one of a virus, bacteria, spore, toxin, or combination thereof; and
the solution applicator is configured to apply at least one of ammonium hydroxide and tris-carbonate or a combination thereof as the basic solution.

18. The system as in claim 1, wherein the digester-medium applicator is configured to apply to the sample at least one of trypsin, subtilisin, chymotrypsin, pepsin, papain, *S. aureus* V8, elastase, Lys-C endoproteinase, Arg-C endoproteinase, and Glu-C endoproteinase enzymes, or combination of these enzymes.

19. The system as in claim 1, wherein the at least one heating device comprises at least one of a hot plate, a radiative heater, a light heater, a laser heater, or a microwave heater.

20. The system as in claim 1, wherein the support comprises:
at least one of a MALDI support or a MALDI target plate.

21. The system as in claim 20, wherein the support comprises:
at least one of a gold surface, a silver surface, a polymer surface, a hydrophobic surface, a hydrophilic surface, a polytetrafluoroethane surface, a metallic surface, a dielectric surface, a stainless steel surface, or a combination thereof.

22. The system as in claim 1, further comprising:
a solvent applicator configured to apply to the sample a solvent for dissolution of contaminants in the sample; and
a solvent removal device configured to remove the applied solvent from the sample and thereby remove at least a part of the contaminants.

23. The system as in claim 1, further comprising:
a processor configured to compare mass analysis data from the sample with a protein sequence database.

24. The system as in claim 23, wherein the processor is configured to compare the mass analysis data to known microorganism protein/peptide sequences or genomic sequences to thereby identify a microorganism.

25. The system as in claim 24, wherein the processor is configured to match the at least one biomarker with results generated from a proteomic interpretation of a microorganism proteome/genome.

26. The system as in claim 1, further comprising:
said organic sample including at least one of a biological agent, a microorganism, a cell culture, a protein sample, a peptide sample, an oligosaccharide sample, a DNA sample, a RNA sample, a lipid sample, a phospholipids sample, a spore, a bacteria, a virus, a toxin, or a combination thereof.

* * * * *